United States Patent [19]

O'Quinn et al.

[11] Patent Number: 5,520,638
[45] Date of Patent: May 28, 1996

[54] MAIN PUMP TUBING FOR ARTHROSCOPY INFUSION PUMP

[75] Inventors: Philip S. O'Quinn, Naples, Fla.; Dennis D. Donnermeyer, Portsmouth, N.H.

[73] Assignee: Arthrex, Inc., Naples, Fla.

[21] Appl. No.: 411,508

[22] Filed: Mar. 28, 1995

[51] Int. Cl.⁶ .................................................. A61M 1/00
[52] U.S. Cl. .................................................. 604/67
[58] Field of Search .................... 128/DIG. 12, DIG. 13; 604/65–67, 27–34

[56] References Cited

U.S. PATENT DOCUMENTS

| | | | |
|---|---|---|---|
| 4,444,198 | 4/1984 | Petre | 604/30 |
| 4,826,482 | 5/1989 | Kamen | 128/DIG. 13 |
| 4,935,005 | 6/1990 | Haines | 604/30 |
| 4,998,914 | 3/1991 | Wiest et al. | 128/DIG. 13 |
| 5,087,245 | 2/1992 | Doan | 128/DIG. 12 |
| 5,098,387 | 3/1992 | Wiest et al. | 604/153 |
| 5,152,746 | 10/1992 | Atkinson et al. | 604/67 |

FOREIGN PATENT DOCUMENTS

| | | |
|---|---|---|
| 3338758 | 5/1985 | Germany . |
| 8600534 | 1/1986 | WIPO . |
| 8705225 | 9/1987 | WIPO | 128/DIG. 12 |

Primary Examiner—John D. Yasko
Assistant Examiner—Manuel Mendez
Attorney, Agent, or Firm—Ostrolenk, Faber, Gerb & Soffen

[57] ABSTRACT

An arthroscopy pump tubing set for delivering a sterile fluid under pressure to a patient undergoing arthroscopic surgery. The tubing set is installed on a peristaltic arthroscopy pump. Fluid is delivered under pressure from fluid bags to a patient, through supply tubing of the tubing set, to achieve better visualization of the operative site. A chamber with a fixed volume is attached to the fluid supply tubing, and a collapsible bladder is contained within the chamber. The collapsible bladder has an open end connected with tubing to a pressure transducer inside the arthroscopy pump. Once activated, the pump begins to introduce sterile fluid from the bags, through the tubing, and into the patient. As pressure builds within the operative site, fluid enters the chamber, and air in the chamber is compressed. The compressed air in the chamber compresses the bladder. Air pressure in the bladder is experienced by the pressure transducer inside the arthroscopy pump. The bladder transmits the pressure in the chamber to the transducer, and isolates the transducer from the sterile fluids and the patient. The transducer feeds pressure information back to the pump, the pump responding to the transducer feedback to control the fluid pressure in the operative site.

6 Claims, 3 Drawing Sheets

5,520,638

MAIN PUMP TUBING FOR ARTHROSCOPY INFUSION PUMP

BACKGROUND OF THE INVENTION

1. Field of the Invention

The present invention relates to a system for delivering a fluid medium to an operative site, while also sensing the pressure of the delivered fluid.

2. Description of the Related Art

During arthroscopic surgery, it is necessary to have a clear field of vision, which requires reduction of blood flow into the operative site, quick removal of debris, and distension of joint spaces sufficient to maneuver surgical instruments. Fluids introduced under pressure into the operative site achieve these objectives.

Prior art fluid-delivery systems typically utilize one tube to deliver fluid under pressure to the operative site, and a second tube to access and measure pressure within the operative site. These systems require: i) an additional incision to access the operative site; and/or ii) additional instruments to measure the pressure at the operative site.

One prior art system, which does not require an additional incision, uses a set of tubes installed on an arthroscopy pump. An air chamber minimizes sudden pressure and flow variations. A pressure transducer is connected to a port on the chamber, and an electrical pin-connector conducts impulses from the transducer to feed pressure information back to the pump. The pump responds by adjusting the pressure.

A problem with this prior art system is that the transducer must be replaced whenever the tubing set is replaced, which results in an unnecessary, extra expense. In addition, the transducer can be lost or contaminated, in which case the entire tubing set must be replaced. Thus, the need exists for an arthroscopy pump tubing set which does not require a separate, external transducer and is thus more economical.

SUMMARY OF THE INVENTION

The present invention overcomes the problems of the prior art by providing an arthroscopy pump tubing set that delivers a fluid medium to an operative site without additional incisions, and without an external transducer for measuring pressure in the operative site. The tubing set is economical, and fluids are delivered without sudden increases and decreases in flow and pressure.

The arthroscopy pump tubing set of the present invention includes a chamber with a fixed, internal air volume. A collapsible bladder is enclosed within the chamber. When fluid under pressure from the arthroscopy pump enters the chamber, air inside the chamber is compressed. The compressed air in the chamber, in turn, compresses the bladder and the air contained within the bladder. The bladder has an open end which is connected outside the chamber to a transducer disposed within the arthroscopy pump. The transducer provides a quantitative measure of the pressure in the tubing system. Advantageously, the pressure transducer is isolated from the sterile fluids and the patient by the collapsible bladder. Thus, the transducer cannot contact the sterile surgical fluids.

The chamber dampens pressure peaks and valleys that may be caused by pump operation. Initial impulses in fluid flow are absorbed and dampened in the chamber, whereby a more constant pressure is sustained in the operative site. A less turbulent environment within the operative site is thus maintained.

Other features and advantages of the present invention will become apparent from the following description of the invention which refers to the accompanying drawings.

DETAILED DESCRIPTION OF THE PREFERRED EMBODIMENT

Figure 1:
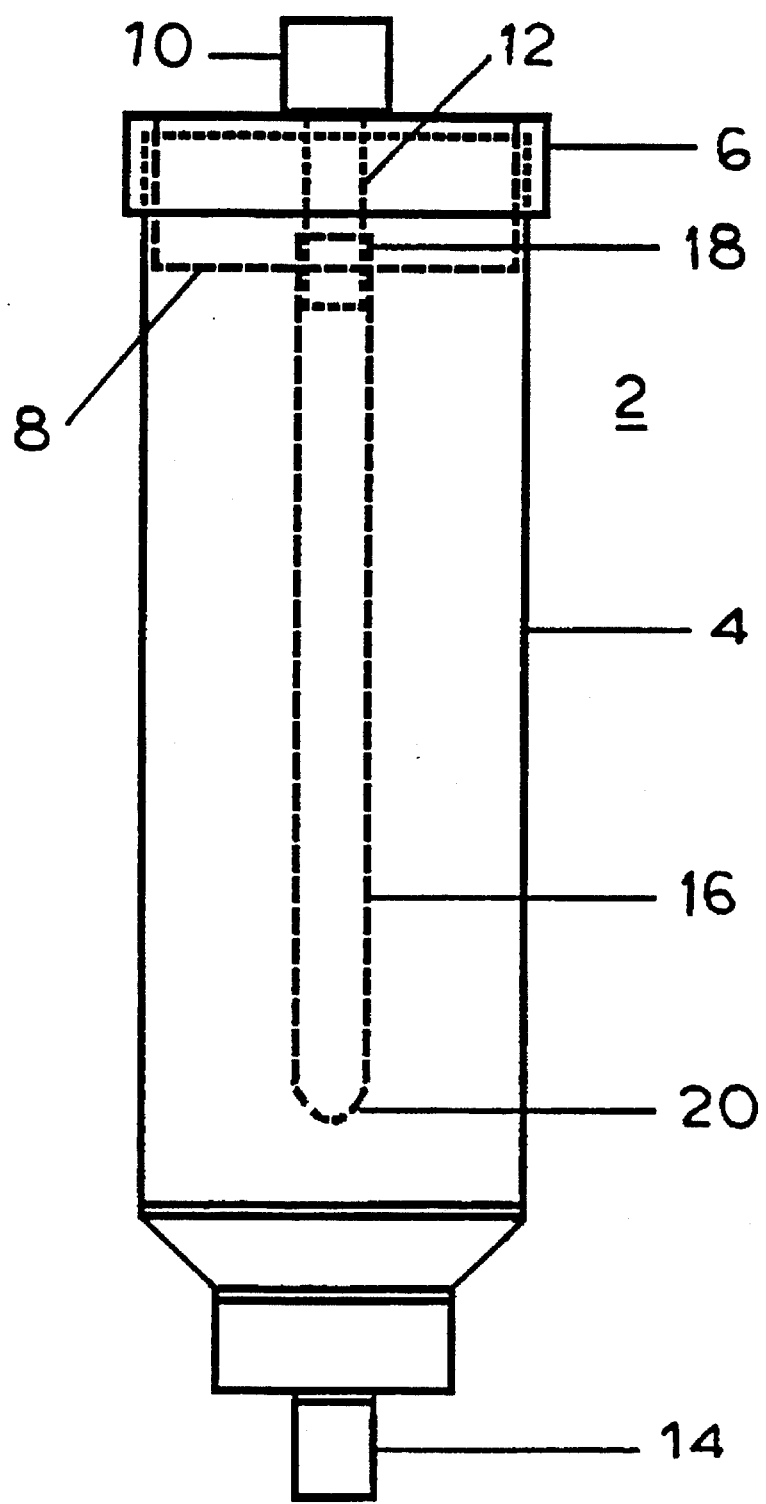
FIG. 1 shows the drip chamber of the present invention, including the collapsible bladder contained therein.

Referring first to FIG. 1, the present invention includes a drip chamber 2, formed of a drip-chamber barrel 4 enclosed by a drip-chamber cover 6. Cover 6 includes flange 8 which cooperates with drip chamber barrel 4 to provide an airtight seal between cover 6 and barrel 4. Cover 6 also includes an outlet port 10, which is adapted to receive a piece of connective tubing, an end of which is inserted in an airtight manner within the port. Outlet port 10 has an extension 12 which reaches into chamber 2. Drip-chamber barrel 4 has a tapered end 14 which is adapted at one end to receive a section of tubing inserted therein to provide an airtight manner.

According to a preferred embodiment of the present invention, drip chamber 2 is manufactured from plastic, preferably, polyvinyl chloride (PVC), which is colorless and clear to allow visualization of the interior of the chamber. Barrel 4 is formed of soft PVC, and cover 6 is made of semi-rigid PVC. Such drip chamber assemblies are available commercially from Haemotronic.

A bladder 16 is enclosed within chamber 2. Bladder 16 has an open end 18 connected in an airtight fashion to extension 12 of outlet port 10. Bladder 16 extends into chamber 2 and terminates at closed end 20. Bladder 16 is a full radius latex sleeve, available commercially from Abbott Labs. According to a preferred embodiment of the present invention, the sleeve measures 0.250"×0.270"×3.5". The bladder and drip chamber are connected to the remainder of the arthroscopy tubing set, described below.

Figure 2:
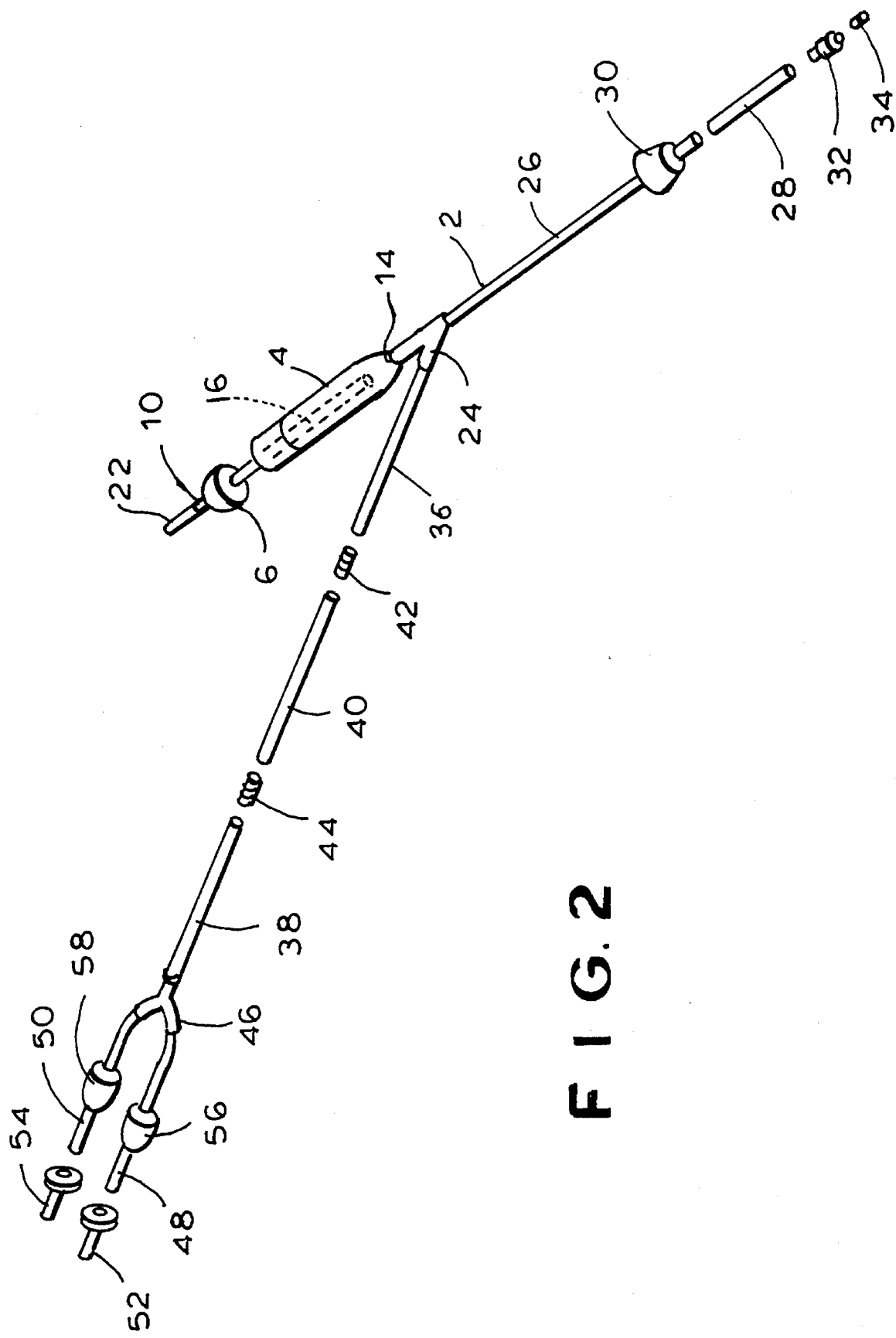
FIG. 2 shows the complete arthroscopic pump tubing set of the present invention.

FIG. 2 shows an exploded view of the complete arthroscopic pump tubing set of the present invention. The tubing used throughout the set is preferably clear PVC plastic. Bladder 16 is connected to drip chamber cover 6 for enclosure within drip-chamber barrel 4. A section of tubing 22 is attached to outlet port 10 for airtight connection to the sensor input of an arthroscopy pump, described in further detail below.

A T- or Y-connector 24 is attached to an inlet port at the tapered end 14 of drip chamber barrel 4. One arm of connector 24 connects through a patient-side tubing section 26 to an adaptor tubing section 28, the fluid flow through which is controlled by a clamp 30. Patient-side tubing section 26 preferably measuring 0.189"× 267"×12.0", and connects to an adaptor section 28, formed of PVC tubing of 55 durometer, which is 0.250"× 375"×4.0". Section 28 terminates at a male luerlock 32, which is covered with a luer protector 34.

The other arm of connector 24 leads through a pump-side tubing section 36, preferably measures 0.189"× 0.267"× 132.0". Pump-side section 36 connects to a section of solution-supply tubing 38 via a pump boot 40. Fluid connection to pump boot 40 is made through a pair of transition reducer connectors 42, 44. Pump boot 40, made of 55 durometer PVC tubing, and measuring 0.250"× 0.375"× 11.0", is adapted to be installed around a set of pump plate rollers on a peristaltic pump, as described in conjunction with FIG. 3, below.

Surgical fluid solutions are supplied to pump boot 40 through a solution supply connector 46. Supply connector 46 couples with two or more spike tubing sections 48, 50, equipped with a pair of spikes 52, 54, respectively, for attachment to fluid supply bags.

Figure 3:
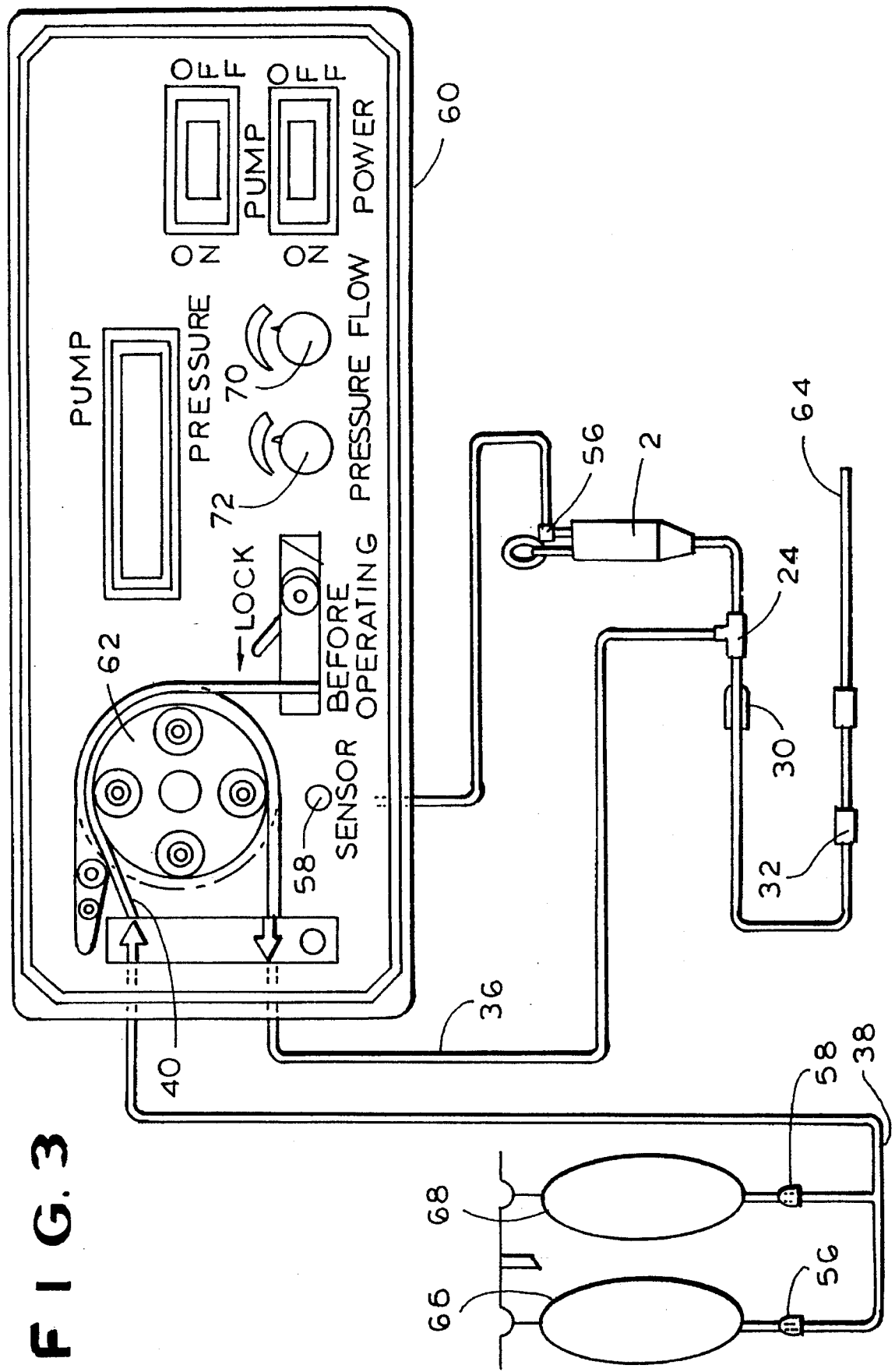
FIG. 3 shows the arthroscopy pump tubing set connected to an arthroscopy pump.

FIG. 3 illustrates the installation of the arthroscopy pump tubing system onto an arthroscopy pump according to a preferred embodiment of the present invention. Chamber 2 is connected via a fitting 56 to a pressure-sensor input 58 of an arthroscopy pump 60. Pump boot 40 is installed around a set of pump plate rollers 62 of arthroscopy pump 60. Luerlock 32 is exposed for connection to a patient tubing system 64.

Intermediate connections between the bladder and the transducer create a chamber which is air-tight and fluid-tight. Thus, the pressure transducer senses the pressure within the attached tubing set and the operative site, without direct exposure of the transducer to either the sterile fluids, or the patient.

With the tubing system installed as shown, arthroscopy pump 60 delivers fluid solution under pressure to the patient from a pair of fluid supply bags 66, 68. As described below, pressure which is experienced in chamber 2 by bladder 16 is transmitted through sensor input 58 to a pressure transducer section inside arthroscopy pump 60.

The operation of the tubing set and pump will now be described.

First, the arthroscopy pump is set to provide a predetermined fluid flow rate at a predetermined pressure. Adjustment of the pressure and flow rate is accomplished via adjusting knobs 70 and 72, respectively. When fluid flows through the tubing system, it initially bypasses the chamber 2 and enters the operating site through patient tubing system 64.

As pressure increases within the operating site, fluid begins to fill chamber 2. Air contained within chamber 2 is compressed and bladder 16 begins to collapse. In turn, air isolated from the chamber within bladder 16 is also compressed. Bladder 16 is in airtight connection with sensor input 58. Increased air pressure within the bladder is sensed by the pressure transducer within the arthroscopy pump. Thus, the pressure in the operational site is transmitted to, and registered by, the transducer in the arthroscopy pump, while the transducer remains isolated from the sterile fluids and the patient. When the pressure transducer within the pump detects a pressure equal to the predetermined pressure, pump 60 will cease operation, until the actual pressure falls below the predetermined pressure.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An arthroscopy pump tubing set, comprising:
   fluid supply tubing for introducing fluid from a fluid source into a patient's body;
   a connector having first, second and third legs, the first and second legs being connected to the fluid supply tubing;
   a chamber having an inlet port and an outlet port, the inlet port being connected to the third leg of the connector so as to be in fluid contact with the fluid supply tubing, the chamber having a fixed volume; and
   a bladder contained within the chamber and covering the outlet port, the bladder sealing the outlet port of the chamber such that the chamber is in closed-ended connection with the fluid supply tubing, the bladder having a variable volume for holding air, the bladder volume being reduced in response to increased pressure within the chamber.

2. The pump tubing set of claim 1, wherein the outlet port in the chamber is for connecting the variable volume of the bladder to a pressure transducer in an air-tight manner such that changes in air pressure within the bladder due to changes in the variable volume of the bladder can be sensed by the transducer.

3. The pump tubing set of claim 2, wherein the bladder is a latex tube having an open end and a closed end, the open end of the tube being in fluid connection with the outlet port of the chamber.

4. An arthroscopy pump tubing set, comprising:
   tubing for supplying fluid from a source into a patient's body;
   a chamber having an inlet port and an outlet port, the inlet port being connected to the tubing, the chamber having a fixed interior volume in fluid contact through the inlet port with the tubing, and the outlet port being open to the outside of the chamber; and
   a collapsible bladder for holding air, the collapsible bladder being contained within the chamber and connected to the outlet port of the chamber for making the chamber closed-ended so as to trap air within the chamber, and for collapsing in response to changes in pressure inside the chamber and transmitting the changes to the outside of the chamber.

5. The pump tubing set of claim 4, wherein the collapsible bladder is a latex tube having an open end and a closed end, the open end being connected to the outlet port.

6. An arthroscopy fluid delivery system, comprising:
   an arthroscopy pump, the arthroscopy pump including a set of peristaltic pump plate rollers, and a pressure transducer; and
   a pump tubing set installed on the set of pump plate rollers, the pump tubing set comprising:
   fluid supply tubing for introducing fluid from a fluid source into a patient's body;
   a chamber in closed-ended fluid contact with the fluid supply tubing, the chamber having a fixed volume for containing fluid and air to be trapped inside the chamber; and
   a bladder contained within the chamber, the bladder containing air and having a variable volume that is reduced in response to increased pressure within the chamber.

* * * * *